(12) United States Patent
Bleicher et al.

(10) Patent No.: US 6,596,743 B2
(45) Date of Patent: Jul. 22, 2003

(54) CARBAMIC ACID DERIVATIVES

(75) Inventors: Konrad Bleicher, Freiburg (DE); Vincent Mutel, Mulhouse (FR); Eric Vieira, Allschwil (CH); Jürgen Wichmann, Steinen (DE); Thomas Johannes Woltering, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/008,827

(22) Filed: Dec. 10, 2001

(65) Prior Publication Data

US 2002/0091150 A1 Jul. 11, 2002

Related U.S. Application Data

(62) Division of application No. 09/545,622, filed on Apr. 10, 2000, now Pat. No. 6,462,198.

(30) Foreign Application Priority Data

Apr. 20, 1999 (EP) .............................. 99107843

(51) Int. Cl.$^7$ ...................... A61K 31/421; C07D 263/48
(52) U.S. Cl. ...................... 514/364; 514/377; 548/131; 548/133; 548/143; 548/233
(58) Field of Search .................. 548/131, 133, 548/143, 233; 514/377, 364

(56) References Cited

U.S. PATENT DOCUMENTS 5,563,278 A * 10/1996 Lifer et al. ................. 548/253

FOREIGN PATENT DOCUMENTS

EP          849 263        6/1998

OTHER PUBLICATIONS

Schlaeger et al., New Dev. New Appl. Anim. Cell Techn. Proc. ESACT Meeting, pp. 105–112 and 117–120.
Behringer et al., *Darstelklung von Diary (3–phenyl–1,2, 4–triazol–5–yl) methanolen*, Justus Liebigs Annalen Der chemie,No. 7/8, pp. 1264–1271 (1975).
Hohenlohe–Oehringen,Reaktionen des 5,5–diphenyl–4–hydroxy–1,2,3–triaazols, Monatshefte Für Chemie, vol. 89, No. 4/5, pp. 588–596 (1958).
Casagrande et al., *Synthesis and antiarrhythmic activity of 5,5–disubstituted–3–aminoalkylhydantoins and some heterocyclic and noncyclic analogues*, IL Farmaco–Edizione Scientifica, vol. 29, No. 10, pp. 757–785 (1974).
Chemical Abstract of Japanese Patent No. 39 012921 (Jul. 8, 1964).
Toms et al., *Latest eruptions in metabotropic glutamate receptors*, Trends in Pharmacological Sciences, vol. 17, No. 12, pp. 429–435 (1996).
Abstract of Document C3, (Hohenlohe–Oehringen, *Monatshefte Für Chemie*, vol. 89, No. 4/5, pp. 588–596 (1958)).

* cited by examiner

*Primary Examiner*—Robert Gerstl
(74) *Attorney, Agent, or Firm*—George W. Johnston; Patricia S. Rocha-Tramaloni; Lyman H. Smith

(57) ABSTRACT

The present invention is a compound of formula:

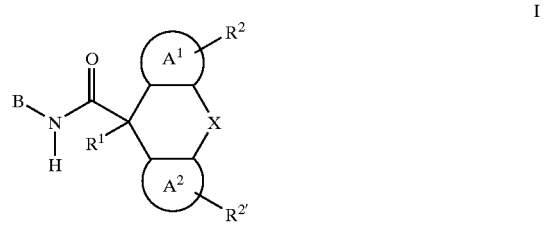

wherein $R^1$, $R^2$, $R^{2'}$, X, $A^1/A^2$ and B are as defined in the specification.

These compounds may be used in the control or prevention of acute and/or chronic neurological disorders such as restricted brain function caused by bypass operations or transplants, poor blood supply to the brain, spinal cord injuries, head injuries, hypoxia caused by pregnancy, cardiac arrest, hypoglycaemia, Alzheimer's disease, Huntington's chorea, ALS, dementia caused by AIDS, eye injuries, retinopathy, cognitive disorders, memory deficits, schizophrenia, idiopathic parkinsonism or parkinsonism caused by medicaments as well as conditions which lead to glutamate deficiency functions, such as e.g. muscle spasms, convulsions, migraine, urinary incontinence, nicotine addiction, psychoses, opiate addiction, anxiety, vomiting, acute and chronic pain, dyskinesia and depression.

19 Claims, No Drawings

CARBAMIC ACID DERIVATIVES

This application is a divisional application of U.S. patent application Ser. No. 09/545,622, filed Apr. 10, 2000 and now U.S. Pat. No. 6,462,198.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs' are known and of these some even have sub-types. On the basis of structural parameters, the different second messenger signalling pathways and the different affinity to low-molecular weight chemical compounds, these eight receptors can be sub-divided into three sub-groups:

mGluR1 and mGluR5 belong to group I;

mGluR2 and mGluR3 belong to group II; and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depression.

SUMMARY OF THE INVENTION

The present invention is concerned with carbamic acid ester derivatives of the formula:

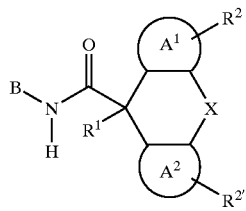

wherein $R^1$ signifies hydrogen or lower alkyl;

$R^2, R^{2'}$ signify, independently from each other, hydrogen, lower alkyl, lower alkoxy, halogen or trifluoromethyl;

X signifies O, S or two hydrogen atoms not forming a bridge;

$A^1/A^2$ signify, independently from each other, phenyl or a 6-membered heterocycle containing 1 or 2 nitrogen atoms;

B is a group of formula:

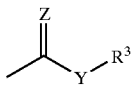

wherein $R^3$ signifies lower alkyl, lower alkenyl, lower alkinyl, benzyl, lower alkyl-cycloalkyl, lower alkyl-cyano, lower alkyl-pyridinyl, lower alkyl-lower alkoxy-phenyl, lower alkyl-phenyl, which is optionally substituted by lower alkoxy, or phenyl, which is optionally substituted by lower alkoxy, or lower alkyl-thienyl, cycloalkyl, lower alkyl-trifluoromethyl or lower alkyl-morpholinyl;

Y signifies —O—, —S— or a bond;

Z signifies —O— or —S—;

or B is a 5-membered heterocyclic group of formulas:

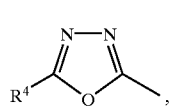

(a)

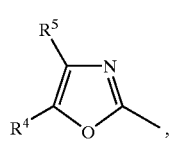

(b)

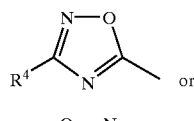

(c)

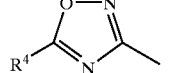

(d)

wherein $R^4$ and $R^5$ signifies hydrogen, lower alkyl, lower alkoxy, cyclohexyl, lower alkyl-cyclohexyl or trifluoromethyl, with the proviso that at least one of $R^4$ or $R^5$ has to be hydrogen; as well as with their pharmaceutically acceptable salts.

In particular, the invention relates to compounds of the following structures:

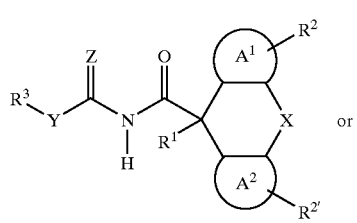

IA or

-continued

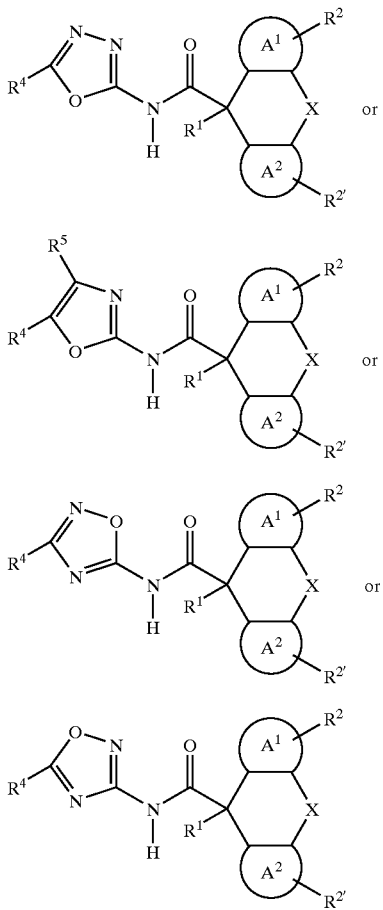

wherein the definition of substituents is given above.

These compounds and their salts are novel and are distinguished by valuable therapeutic properties.

It has surprisingly been found that the compounds of formula I are metabotropic glutamate receptor modulators, acting as antagonists or agonists.

Objects of the present invention are compounds of formula I and their pharmaceutically acceptable salts per se and as pharmaceutically active substances, their manufacture, medicaments based on a compound in accordance with the invention and their production as well as the use of the compounds in accordance with the invention in the control or prevention of illnesses of the aforementioned kind, and, respectively, for the production of corresponding medicaments.

DETAILED DESCRIPTION OF THE INVENTION

Preferred compounds of formula I in the scope of the present invention are those, in which A signifies phenyl, X signifies 2 hydrogen atoms not forming a bridge and B signifies the group:

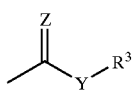

wherein Z is O and $R^3$ and Y are described above.

The following are examples of such compounds:

diphenylacetyl-carbamic acid butyl ester, diphenylacetyl-carbamic acid ethyl ester or diphenylacetyl-carbamic acid pent-4-ynyl ester.

Compounds of formula I, wherein A signifies phenyl, X signifies —O— or —S— and B signifies the group:

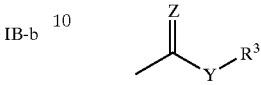

are further preferred, wherein Z is O and $R^3$ and Y are described above.

Examples of such compounds are:

(9H-xanthene-9-carbonyl)-carbamic acid ethyl ester, (9H-xanthene-9-carbonyl)-carbamic acid butyl ester or (9H-thioxanthene-9-carbonyl)-carbamic acid butyl ester.

Preferred compounds of formula I in the scope of the present invention are those, in which A signifies phenyl, X signifies 2 hydrogen atoms not forming a bridge and B signifies a heterocyclic group of the formulas:

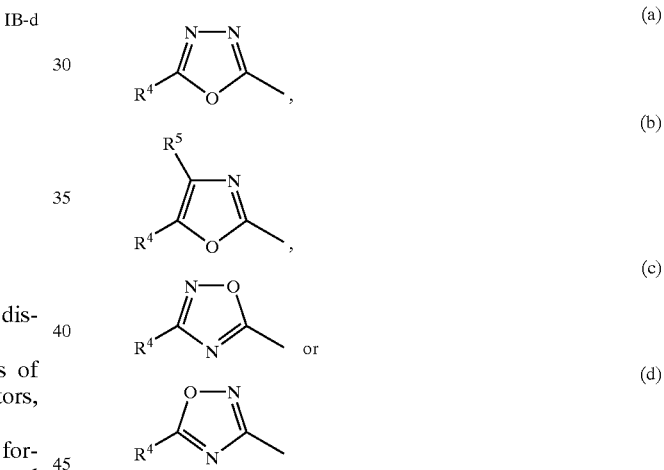

wherein $R^4$ and $R^5$ have the significances given above.

Examples of such compounds are:

N-(5-ethyl-oxazol-2-yl)-2,2-diphenyl-acetamide,

N-(5-methyl-oxazol-2-yl)-2,2-diphenyl-acetamide, 2,2-diphenyl-N-(5-propyl-[1,3,4]oxadiazol-2-yl)-acetamide, N-[5-(2-methoxy-ethyl)-[1,3,4]oxadiazol-2-yl]-2,2-diphenyl-acetamide, N-(3-methyl-[1,2,4]oxadiazol-5-yl)-2,2-diphenyl-acetamide, N-(3-cyclopropyl-[1,2,4]oxadiazol-5-yl)-2,2-diphenyl-acetamide or N-(5-methyl-[1,2,4]oxadiazol-3-yl)-2,2-diphenyl-acetamide.

Preferred are further compounds of formula I, in which A signifies phenyl, X signifies —O— or —S—; and B signifies a heterocyclic group of the formulas:

(a) 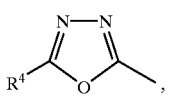

(b) 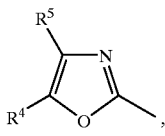

(c) 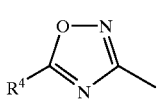 or (d) 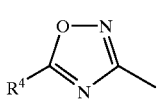

for example the following compounds:

9H-xanthene-9-carboxylic acid oxazol-2-yl-amide, 9H-xanthene-9-carboxylic acid (5-propyl-[1,3,4]oxadiazol-2-yl)-amide, 9H-xanthene-9-carboxylic acid (5-ethyl-oxazol-2-yl)-amide, 9H-xanthene-9-carboxylic acid (5-methyl-oxazol-2-yl)-amide, 9H-xanthene-9-carboxylic acid (5-propyl-oxazol-2-yl)-amide, 9H-xanthene-9-carboxylic acid (5-ethyl-[1,3,4]oxadiazol-2-yl)-amide, 9H-xanthene-9-carboxylic acid (5-cyclopropylmethyl-[1,3,4]oxadiazol-2-yl)-amide, 9H-xanthene-9-carboxylic acid (4-methyl-oxazol-2-yl)-amide, 9H-xanthene-9-carboxylic acid (3-methyl-[1,2,4]oxadiazol-5-yl)-amide, 9H-Xanthene-9-carboxylic acid (5-trifluoromethyl-[1,3,4]oxadiazol-2-yl)-amide, 9H-Xanthene-9-carboxylic acid (5-methoxymethyl-[1,3,4]oxadiazol-2-yl)-amide, 9H-xanthene-9-carboxylic acid (3-cyclopropyl-[1,2,4]oxadiazol-5-yl)-amide or 9H-xanthene-9-carboxylic acid (5-methyl-[1,2,4]oxadiazol-3-yl)-amide.

The invention embraces all stereoisomeric forms in addition to the racemates.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkoxy" denotes a lower alkyl residue in the sense of the foregoing definition bonded via an oxygen atom.

The term "halogen" embraces fluorine, chlorine, bromine and iodine.

The compounds of formula I and their pharmaceutically acceptable salts can be manufactured by processes, which comprises reacting a compound of the formula:

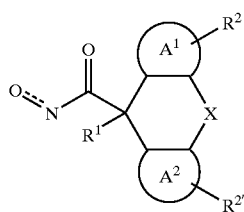  II with a compound of the formula:

$R^3{-}YH$  III to a compound of formula:

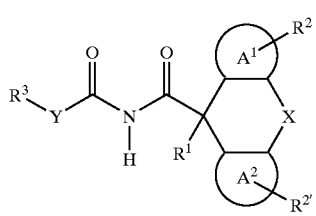  IA-1 wherein the substituents have the significances given above, or b) reacting a compound of formula:

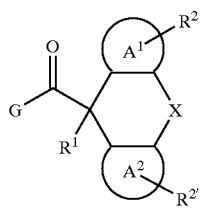  IV with a compound of the formula:

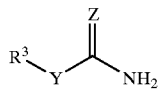  V to a compound of formula:

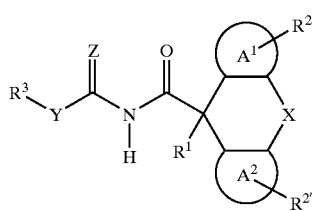  IA in which G is a suitable leaving group, such as Cl, Br or acyloxy, or a carbonyl chloride equivalent such as a carbonyl-pyrazolide, carbonyl imidazole, carbonyl benzotriazole, carbonyloxysuccinimide, or activated esters such as p-nitrophenylester, pentachlorophenylester and the like, and the other substituents have the significances given above, c) or reacting a compound of formula:

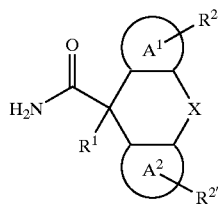

VI with a compound of the formula:

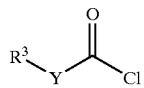

to a compound of formula:

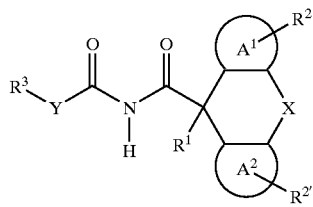

IA-1 or d) reacting a compound of formula:

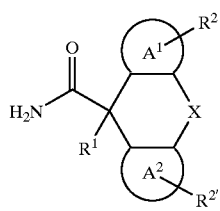

VI with a compound of the formula:

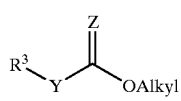

VIII to a compound of formula:

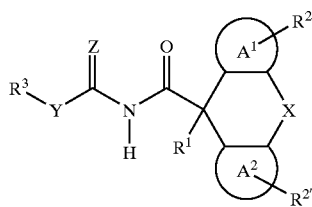

IA wherein the substituents have the significances set forth above, or e) reacting a compound of formula:

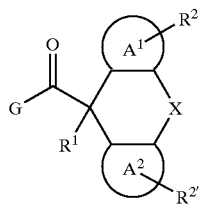

IV with a heterocyclic compound of formula

B—NH$_2$   IX to give a compound of formula:

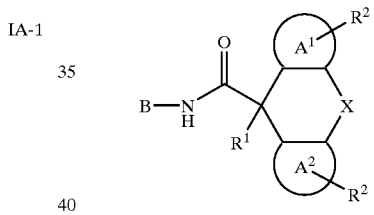

IB (a–d)

wherein B is a 5-membered heterocycle of the formulas:

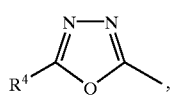

(a)

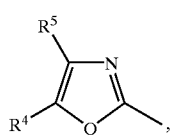

(b)

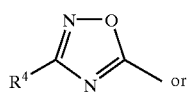

(c)

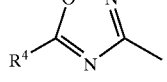

(d)

and wherein the remaining substituents have the significances given above, and, if desired, converting a functional group in a compound of formula I into another functional group and, if desired, converting a compound of formula I into a pharmaceutically acceptable salt.

In accordance with process variant a) to a compound of formula III, for example an alcohol (1-butanol, benzyl alkohol, allyl alkohol, isopropyl-alkohol) in dichloromethane is added a compound of formula II, for example diphenylacetyl isocyanate and the mixture is stirred at room temperature.

Compounds of formula IA may be prepared in accordance with process variant b). A compound of formula V, for example a corresponding urethane or carbamic acid alkyl ester, is reacting with a compound of formula IV, for example with 9H-xanthene-9-carbonyl chloride or bromide, or with an acyloxy derivative of formula IV, or with a carbonyl chloride equivalent of formula IV, which compounds contain a carbonyl-pyrazolide group, a carbonyl imidazole group, a carbonyl benzotriazole group, a carbonyloxysuccinimide group or an activated ester such as p-nitrophenylester, pentachlorophenylester and the like. This reaction is carried out in a solvent, such as pyridine, at room temperature by methods known in the art.

Furthermore, compounds of formula IA-1 and IA may be prepared in accordance with process variant c) and d), wherein a compound of formula VI is reacting with a compound of formula VII or VIII. This reaction is carried out similar to those, described for process variant b). Compounds of formula IB may be prepared by a reaction of a heterocyclic compound of formula IX with a compound of formula IV in the presence of N,N-dimethylamino pyridine at a temperature of 0° C. The preferred solvent is methylene chloride.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds.

Scheme 1 gives an overview of the manufacture of the compounds of formula IA. The manufacture of representative compounds of formula I is described in detail in examples 1–30, 32 and 34–43. Scheme 2 describes the process of manufacture of compounds of formula IB, which process is described in more detail in examples 31, 33 and 44–69.

Scheme 1

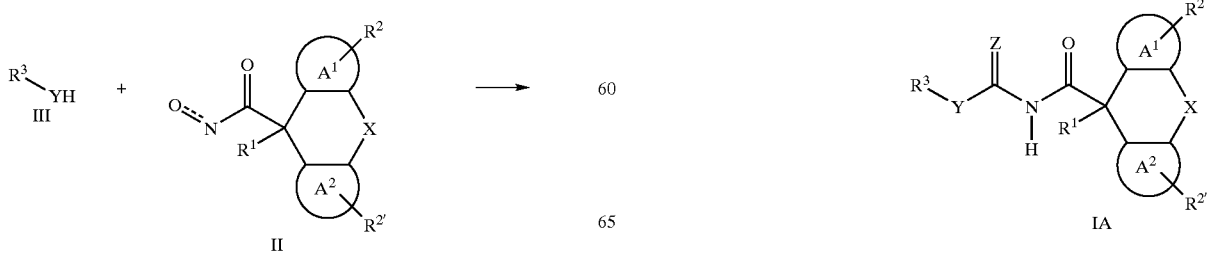

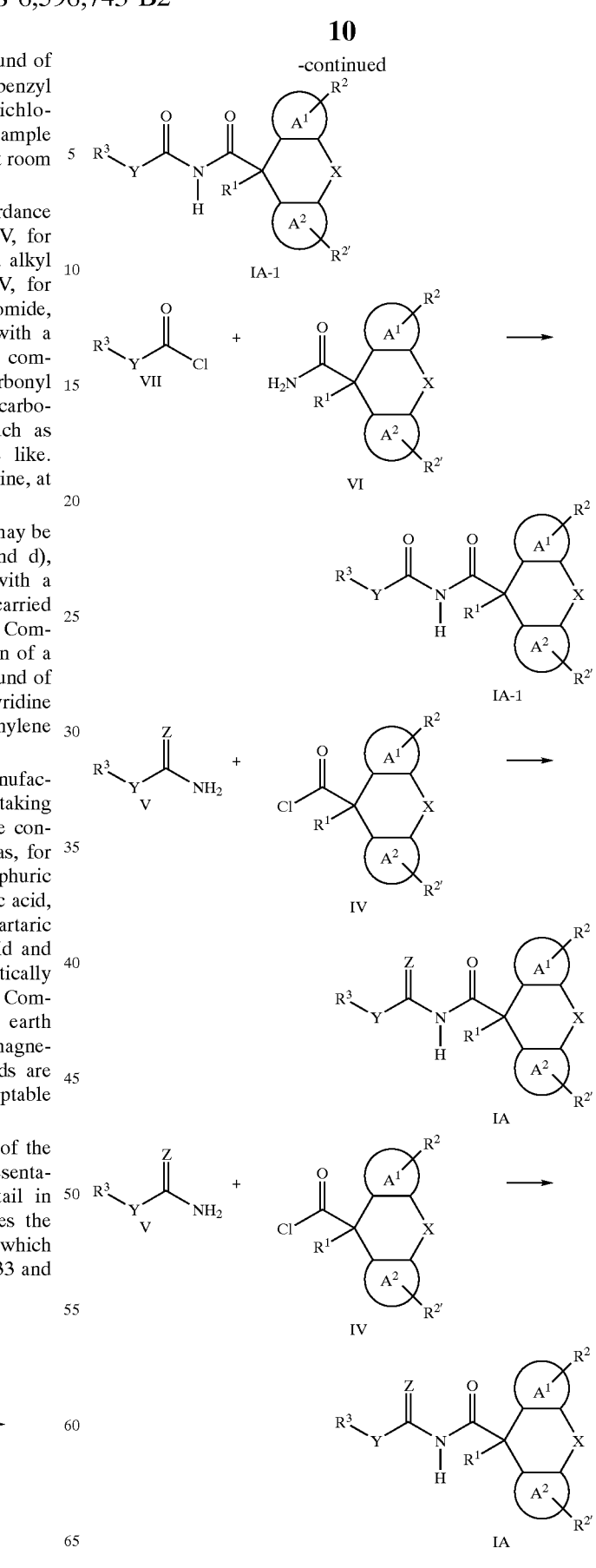

The substituents have the significances given earlier.

Scheme 2

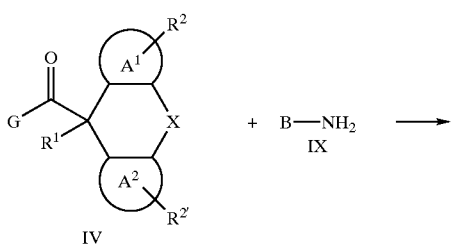

wherein B is a 5-membered heterocyclic compound of formulas:

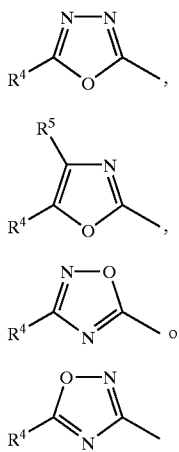

and the remaining definitions of substituents are given above.

The starting materials used in schemes 1 and 2 are known compounds or may be prepared by methods known per se.

The compounds of formula I and their pharmaceutically acceptable salts are, as already mentioned above, metabotropic glutamate receptor agonists and/or antagonists and can be used for the treatment or prevention of acute and/or chronic neurological disorders, such as psychosis, schizophrenia, Alzheimer's disease, cognitive diorders and memory deficits, as well as acute and chronic pain. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Alzheimer's disease, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of the present invention are group I mGlu receptor agonists and/or antagonists. For example, it has been shown that the compounds of examples 1–22 and 30–69 show agonistic activities and those of examples 23–29 are antagonists. The compounds show activities, as measured in the assay described below, of 50 $\mu$M or less, typically 1 $\mu$M or less, and ideally of 0.5 $\mu$M or less.

In the table below are shown some specific activity-data:

| Example No. | agonist/antagonist | $IC_{50}$ ($\mu$M) |
| --- | --- | --- |
| 10 | agonist | 0.22 |
| 32 | agonist | 0.14 |
| 65 | agonist | 0.4 |
| 23 | antagonist | 6.31 |
| 24 | antagonist | 2.79 |
| 25 | antagonist | 1.38 |

Test Description cDNA encoding rat mGlu 1a receptor obtained from Prof. S. Nakanishi (Kyoto, Japan) was transiently transfected into EBNA cells using a procedure described by Schlaeger et al, New Dev. New Appl. Anim. Cell Techn., Proc. ESACT Meet., 15, (1998), 105–112 and 117–120. [$Ca^{2+}$]i measurements were performed on mGlu 1a transfected EBNA cells after incubation of the cells with Fluo-3 AM (0.5 $\mu$M final concentration) for 1 hour at 37° C. followed by 4 washes with assay buffer (DMEM supplemented with Hank's salt and 20 mM HEPES. [$Ca^{2+}$]i measurements were done using a fluorometric imaging plate reader (FLIPR, Molecular Devices Corporation, La Jolla, Calif., USA). When compounds were evaluated as antagonists they were tested against 10 $\mu$M glutamate as agonist.

The inhibition (antagonists) or activation (agonists) curves were fitted with a four parameter logistic equation giving $EC_{50}$, and Hill coefficient using the iterative non linear curve fitting software Origin (Microcal Software Inc., Northampton, Mass., USA).

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

EXAMPLE 1

Diphenylacetyl-carbamic acid butyl ester

To a stirred solution of 1-butanol (0.32 ml, 3.49 mmol) in dichloromethane (4 ml) was added a solution of diphenylacetyl isocyanate (2.33 ml, 0.5M in $CH_2Cl_2$, 1.16 mmol) and the mixture was stirred at RT for 1 h. Removal of the solvent in vacuum left a yellow oil, which was purified by column chromatography on silica gel (ethyl acetate/hexane 1:2) to give the title compound (0.3 g, 83%) as a light yellow solid, m.p. 82–84° C. and MS: m/e=334 (M+Na$^+$).

EXAMPLE 2

Diphenylacetyl-carbamic acid benzyl ester

The title compound, white solid, m.p. 100–101° C. and MS: m/e=345 (M$^+$) was prepared in accordance with the general method of example 1 from diphenylacetyl isocyanate and benzyl alcohol.

EXAMPLE 3

Diphenylacetyl-carbamic acid allyl ester

The title compound, white solid, m.p. 118–120° C. and MS: m/e=295 (M$^+$) was prepared in accordance with the general method of example 1 from diphenylacetyl isocyanate and allyl alcohol.

EXAMPLE 4

Diphenylacetyl-carbamic acid isopropyl ester

The title compound, white solid, m.p. 122–124° C. and MS: m/e=297 (M$^+$) was prepared in accordance with the general method of example 1 from diphenylacetyl isocyanate and isopropyl alcohol.

EXAMPLE 5

Diphenylacetyl-carbamic acid tert.-butyl ester

The title compound, light yellow solid, m.p. 160–162° C. and MS: m/e=334 (M+Na$^+$) was prepared in accordance with the general method of example 1 from diphenylacetyl isocyanate and tert.-butyl alcohol.

EXAMPLE 6

(9H-Xanthene-9-carbonyl)-carbamic acid ethyl ester

To a stirred solution of urethane (0.82 g, 9.21 mmol) and DMAP (0.05 g, 0.41 mmol) in pyridine (10 ml) was added at 0° C. 9H-xanthene-9-carbonyl chloride (1.50 g, 6.13 mmol). Stirring was continued at RT for 17 h, the reaction mixture was evaporated and water (50 ml)/sat. $NaHCO_3$ solution (20 ml) was added. The solid was filtered off and crystallized from water and afterwards from EtOH/hexane to give the product (1.22 g, 67%) as a white solid, m.p. 228° C. (dec.) and MS: m/e=298.2 (M+H$^+$).

EXAMPLE 7

(RS)-(2-Bromo-9H-xanthene-9-carbonyl)-carbamic acid ethyl ester

The title compound, light brown solid, m.p. 203° C. and MS: m/e=375 (M$^+$) was prepared in accordance with the general method of example 6 from urethane and 2-bromo-9H-xanthene-9-carbonyl chloride.

EXAMPLE 8

(9H-Xanthene-9-carbonyl)-carbamic acid butyl ester

The title compound, white solid, m.p.=180–183° C., MS: m/e=325.4 (M+H$^+$) was prepared in accordance with the general method of example 6 from 9H-xanthene-9-carbonyl chloride and carbamic acid butyl ester.

EXAMPLE 9

Diphenylacetyl-carbamic acid ethyl ester

The title compound, white solid, m.p. 133° C. and MS: m/e=284.2 (M+H$^+$) was prepared in accordance with the general method of example 1 from diphenyl-acetyl isocyanate and ethanol.

EXAMPLE 10

Diphenylacetyl-carbamic acid cyclopropylmethyl ester

The title compound, white solid, m.p.=108° C., MS: m/e=309.4 (M+H$^+$) was prepared in accordance with the general method of example 1 from diphenylacetyl isocyanate and cyclopropyl-methanol.

EXAMPLE 11

Diphenylacetyl-carbamic acid pent-4-ynyl ester

The title compound, white solid, m.p. 109° C. and MS: m/e=321.4 (M+H$^+$) was prepared in accordance with the general method of example 1 from diphenylacetyl isocyanate and pent-4-yn-1-ol.

EXAMPLE 12

Diphenylacetyl-carbamic acid 2-cyano-ethyl ester

The title compound, white solid, m.p. 113° C. and MS: m/e=308.3 (M+H$^+$) was prepared in accordance with the general method of example 1 from diphenylacetyl isocyanate and 3-hydroxy-propionitrile.

EXAMPLE 13

Diphenylacetyl-carbamic acid 3-pyridin-4-yl-propyl ester

The title compound, brown solid, m.p. 147–50° C. and MS: m/e=374.4 (M+H$^+$) was prepared in accordance with the general method of example 1 from diphenylacetyl isocyanate and 3-pyridin-4-yl-propan-1-ol.

EXAMPLE 14

Diphenylacetyl-carbamic acid 3-benzyloxy-propyl ester

The title compound, colorless oil, MS: m/e=403.5 (M+H$^+$) was prepared in accordance with the general method of example 1 from diphenylacetyl isocyanate and 3-benzyloxy-propan-1-ol.

EXAMPLE 15

Diphenylacetyl-carbamic acid 2-(3,4-dimethoxy-phenyl)ethyl ester

The title compound, white solid, m.p. 144° C. and MS: m/e=419.5 (M+H$^+$) was prepared in accordance with the general method of example 1 from diphenylacetyl isocyanate and 2-(3,4-dimethoxy-phenyl)-ethanol.

EXAMPLE 16

Diphenylacetyl-carbamic acid (RS)-2-phenyl-propyl ester

The title compound, white solid, m.p. 131° C. and MS: m/e=373.5 (M+H$^+$) was prepared in accordance with the general method of example 1 from diphenylacetyl isocyanate and (RS)-2-phenyl-propan-1-ol.

EXAMPLE 17

Diphenylacetyl-carbamic acid thien-2-yl methyl ester

The title compound, white solid, m.p. 116° C. and MS: m/e=351.4 (M+H$^+$) was prepared in accordance with the general method of example 1 from diphenylacetyl isocyanate and thien-2-yl-methanol.

EXAMPLE 18

Diphenylacetyl-carbamic acid cyclopentyl ester

The title compound, white solid, m.p. 120–123° C. and MS: m/e=323.4 (MH+) was prepared in accordance with the general method of example 1 from diphenylacetyl isocyanate and cyclopentanol.

EXAMPLE 19

Diphenylacetyl-carbamic acid cyclohexyl ester

The title compound, white solid, m.p. 117–119° C. and MS: m/e 337.4 (M+H$^+$) was prepared in accordance with the general method of example 1 from diphenylacetyl isocyanate and cyclohexanol.

EXAMPLE 20

Diphenylacetyl-carbamic acid 4-phenyl-butyl ester

The title compound, light yellow solid, m.p.=118° C. and MS: m/e=387.5 (M+H$^+$) was prepared in accordance with the general method of example 1 from diphenylacetyl isocyanate and 4-phenyl-butan-1-ol.

EXAMPLE 21

Diphenylacetyl-carbamic acid 3,5-dimethoxy-phenyl ester

The title compound, white solid, m.p.=150–152° C. and MS: m/e=391.4 (M+H$^+$) was prepared in accordance with the general method of example 1 from diphenylacetyl isocyanate and 3,5-dimethoxy-phenol.

EXAMPLE 22

Diphenylacetyl-carbamic acid 2,2,2-trifluoro-ethyl ester

The title compound, white solid, m.p.=125–127° C. and MS: m/e=337.3 (M+H$^+$) was prepared in accordance with the general method of example 1 from diphenylacetyl isocyanate and 2,2,2 trifluoro-ethanol.

EXAMPLE 23

(2.2-Diphenyl-propionyl)-carbamic acid ethyl ester

The title compound, colorless gum, MS: m/e=297.4 (M+H$^+$) was prepared in accordance with the general method of example 1 from crude 2,2-diphenylpropionyl isocyanate and ethanol.

EXAMPLE 24

(2,2-Diphenyl-propionyl)-carbamic acid allyl ester

The title compound, white solid, m.p.=89° C. and MS: m/e=309.4 (M+H$^+$) was prepared in accordance with the general method of example 1 from 2,2-diphenylpropionyl isocyanate and prop-2-en-1-ol.

EXAMPLE 25

(2,2-Diphenyl-propionyl)-carbamic acid butyl ester

The title compound, white solid, m.p.=83° C. and MS: m/e=325.4 (M+H$^+$) was prepared in accordance with the general method of example 1 from 2,2-diphenylpropionyl isocyanate and butan-1-ol.

EXAMPLE 26

(2,2-Diphenyl-propionyl)-carbamic acid cyclopropyl methyl ester

The title compound, white solid, m.p.=125° C. and MS: m/e=323.4 (M+H$^+$) was prepared in accordance with the general method of example 1 from 2,2-diphenylpropionyl isocyanate and cyclopropyl-methanol.

EXAMPLE 27

(2,2-Diphenyl-propionyl)-carbamic acid cyclohexyl ester

The title compound, white solid, m.p.=126° C. and MS: m/e=351.4 (M+H$^+$) was prepared in accordance with the general method of example 1 from 2,2-diphenylpropionyl isocyanate and cyclohexanol.

EXAMPLE 28

(2,2-Diphenyl-propionyl)-carbamic acid 4-phenyl-butyl ester

The title compound, yellow oil, MS: m/e=401.5 (M+H$^+$) was prepared in accordance with the general method of example 1 from 2,2-diphenylpropionyl isocyanate and 4-phenyl-butan-1-ol.

EXAMPLE 29

(2,2-Diphenyl-propionyl)-carbamic acid 2,2,2-trifluoro-ethyl ester

The title compound, white solid, m.p.=143–145° C., MS: m/e=351.3 (M+H$^+$) was prepared in accordance with the general method of example 1 from 2,2-diphenylpropionyl isocyanate and 2,2,2-trifluoro-ethanol.

EXAMPLE 30

(9H-Thioxanthene-9-carbonyl)-carbamic acid ethyl ester

The title compound, white solid, m.p.=179–182° C., MS: m/e=314.2 (M+H$^+$) was prepared in accordance with the general method of example 6 from 9H-thioxanthene-9-carbonyl chloride [U.S. Pat. No. 3,284,449] and urethane.

EXAMPLE 31

9H-Thioxanthene-9-carboxylic acid oxazol-2-ylamide

To a stirred solution of (0.048 g, 0.575 mmol) 2-amino-oxazole [Cockerill & al., Synthesis 591(1976)], and DMAP (0.003 g, 0.03 mmol) in pyridine (2 ml) was added at 0° C. (0.100 g, 0.384 mmol) 9H-thioxanthene-9-carbonyl chloride. Stirring was continued at RT for 16 h, the reaction mixture was evaporated and water (5 ml)/sat. NaHCO$_3$ solution (2 ml) was added. The solid was filtered off, dissolved in dichloromethane, dried (MgSO$_4$), and concentrated in vaccuo. The crude material was purified by column chromatobraphy on silica gel (methylene chloride/methanol 40:1) to give the product (0.022 g, 18%) as a white solid, m.p. 188–191° C. and MS: m/e=309.1 (M+H$^+$).

EXAMPLE 32

(9H-Thioxanthene-9-carbonyl)-carbamic acid butyl ester

The title compound, white solid, m.p. 151–154° C., MS: m/e 342.2 (M+H$^+$) was prepared in accordance with the general method of example 6 from 9H-thioxanthene-9-carbonyl chloride and carbamic acid butyl ester.

EXAMPLE 33

9H-Xanthene-9-carboxylic acid oxazol-2-yl-amide

The title compound, white solid, m.p.=232–235° C., MS: m/e=292 (M$^+$) was prepared in accordance with the general method of example 31 from 9H-xanthene-9-carbonyl chloride and 2-amino-oxazole.

EXAMPLE 34

Diphenylacetyl-carbamic acid 2-morpholin-4-yl-ethyl ester

The title compound, white solid, m.p.=135–137° C. and MS: m/e=369.3 (M+H$^-$) was prepared in accordance with the general method of example 1 from diphenylacetyl isocyanate and 2-morpholin-4-yl-ethanol.

EXAMPLE 35

Diphenylacetyl-thiocarbamic acid S-butyl ester

The title compound, white solid, m.p.=99° C. and MS: m/e=327 (M$^+$) was prepared in accordance with the general method of example 1 from diphenylacetyl isocyanate and butanethiol.

EXAMPLE 36

[(3-Chloro-5-trifluoromethyl-pyridin-2-yl)-m-tolyl-acetyl]-carbamic acid ethyl ester 97 μl (95 mg, 0.80 mmol) Diethylcarbonate and 38 ul (30 mg, 0.50 mmol) isopropanol were dissolved in 2 ml of absolute THF. The solution was cooled to 0° C. and 29 mg (0.67 mmol) sodium hydride dispersion (55% in mineral oil) was added. Then 164 mg (0.50 mmol) 3-chloro-5-trifluoromethyl-2-pyridyl-3-methylphenylacetamide in portions at 0° C. After stirring for 1 h at 0° C., the reaction was allowed to warm up to room temperature and stirred overnight. Workup in the usual manner with ammonium chloride solution and ethyl acetate yielded a yellow oil which was purified by flash chromatography on silicagel using a 5:1 mixture of hexane and ethyl acetate as eluant. One obtains 14.1 mg (0.035 mmol, 7%) of [(3-chloro-5-trifluoromethyl-pyridin-2-yl)-m-tolyl-acetyl]-carbamic acid ethyl ester as a white solid, m.p.=146–147° C., MS: m/e=401.3 (M+H).

EXAMPLE 37

9H-Xanthene-9-carbonyl)-carbamic acid cyclopropylmethyl ester

The title compound, white solid, m.p.=183–185° C., MS: m/e=323 (M$^+$) was prepared in accordance with the general method of example 36 from 9H-xanthene-9-carbonyl chloride and carbamic acid cyclopropylmethyl ester.

EXAMPLE 38

(4-Trifluoromethyl-9H-xanthene-9-carbonyl)-carbamic acid ethyl ester

The title compound, white solid, m.p.=196–198° C., MS: m/e=365 (M$^+$) was prepared in accordance with the general method of example 36 from 4-trifluoromethyl-9H-xanthene-9-carbonyl chloride and carbamic acid ethyl ester.

EXAMPLE 39

Cyclopropanecarboxylic acid diphenylacetyl-amide

To a stirred and cooled (0° C.) solution of 2,2-diphenylacetamide (500 mg, 2.36 mmol) in THF (20 ml) was added sodium hydride (95 mg, 2.36 mmol; 60%) and the mixture was stirred at RT for 0.5 h. Then cyclopropanecarboxylic acid chloride(247 mg, 2.36 mmol) dissolved in THF (5 ml) was added dropwise at RT and the solution was stirred at RT for 20 h. The reaction mixture was poured into sat. NaHCO$_3$ solution (50 ml) and extracted with ethyl acetate (2×70 ml). The combined organic layers were washed with brine (50 ml), dried (MgSO$_4$) and evaporated. Further purification by column chromatography (toluene/ethyl acetate 19:1) yielded the product which was recrystallized from ethyl acetate/hexane to give a white solid (133 mg, 20%), m.p. 178° C. and MS: m/e=279 (M$^+$).

EXAMPLE 40

9H-Xanthene-9-carboxylic acid butyryl-amide

The title compound, white solid, m.p. 222° C. and MS: m/e=295 (M$^+$) was prepared in accordance with the general method of example 39 from 9H-xanthene-9-carboxylic acid amide and propanecarboxylic acid chloride.

EXAMPLE 41

N-Diphenylacetyl-butyramide

The title compound, white solid, m.p. 205° C. and MS: m/e=281 (M$^+$) was prepared in accordance with the general method of example 39 from 2,2-diphenylacetamide and propanecarboxylic acid chloride.

EXAMPLE 42

Pentanecarboxylic acid diphenylacetyl-amide

The title compound, white solid, m.p. 87° C. and MS: m/e=309 (M$^+$) was prepared in accordance with the general method of example 39 from 2,2-diphenylacetamide and pentanecarboxylic acid chloride.

EXAMPLE 43

Pentanoic acid diphenylacetyl-amide

The title compound, white solid, m.p. 83° C. and MS: m/e=296.3 (M+H$^+$) was prepared in accordance with the general method of example 39 from 2,2-diphenylacetamide and butanecarboxylic acid chloride.

EXAMPLE 44

9H-Xanthene-9-carboxylic acid (5-propyl-[1,3,4] oxadiazol-2-yl)-amide

44a) To a solution of 76 mg (0.60 mmol, 1.2 equiv.) 5-propyl-[1,3,4]oxadiazol-2-ylamine and 6 mg (0.05 mmol, 0.1 equiv.) of N,N-dimethylamino pyridine in 2 ml of dry pyridine was added a solution of 122 mg (0.5 mmol) 9-xanthene-carboxylic acid chloride in 1.22 ml of methylene chloride dropwise at 0° C. The mixture was stirred 3–4 h at 0° C. and then at room temperature overnight. The mixture was poured into a well stirred mixture of 50 ml of ethyl acetate and 50 ml of water. The organic phase was separated. The aqueous phase was extracted twice with 25 ml of ethyl acetate. The combined organic phases were washed twice with 25 ml of water, and concentrated. The residue was taken up in c.a. 25 ml of ethyl acetate and evaporated to dryness. The crude product (167 mg, light yellow solid) yielded, after recristallisation from ethanol 62 mg (0.185 mmol, 37%) of 9H-xanthene-9-carboxylic acid (5-propyl-[1,3,4]oxadiazol-2-yl)-amide as white cristals, m.p. 215–216° C. and MS: m/e=335 (M$^+$).

44b) The 5-propyl-[1,3,4]oxadiazol-2-ylamine used in the above reaction was obtained as follows:

To a solution of 5.0 g (47.0 mmol) cyanogen bromide in 50 ml of methanol was added dropwise over a period of 30 min a solution of 4.80 g (47.0 mmol) butyric acid hydrazide in 50 ml of methanol. The mixture was then refluxed for 15 min, and then concentrated in vacuo till cristallisation began. The cristals (9 g) were filtered off, taken up in 60 ml of ethanol. Then 5 g of finely powdered potassium carbonate were added and the suspension was stirred for 5 min at room temperature. The resulting orange suspension was filtered, and the filtrate was concentrated in vacuo. The resulting orange powder (5.5 g) was purified by flash chromatography on silicagel with a 80:10:1 mixture of methylene chloride/methanol/28% ammonia as eluent to yield 3.95 g (31.1 mmol, 66%) of 5-propyl-[1,3,4]oxadiazol-2-ylamine as white cristals, MS: m/e=127 (M$^+$).

EXAMPLE 45

2,2-Diphenyl-N-(5-propyl-[1,3,4]oxadiazol-2-yl)-acetamide

The title compound, viscous oil and MS: m/e=322.4 (M+H$^+$) was prepared in accordance with the general method of example 44a from 5-propyl-[1,3,4]oxadiazol-2-ylamine and 2,2-diphenylacetic acid chloride.

EXAMPLE 46

9H-Xanthene-9-carboxylic acid [1,3,4]oxadiazol-2-ylamide

The title compound, white solid, m.p. 239–240° C. and MS: m/e=293 (M$^+$) was prepared in accordance with the general method of example 44a from [1,3,4]oxadiazol-2-ylamine and 9-xanthene-carboxylic acid chloride. The [1,3,4]oxadiazol-2-ylamine, white solid, MS: m/e=85 (M$^+$) used in the above reaction was prepared in accordance with the general method of example 44b from formic acid hydrazide and cyanogen bromide.

EXAMPLE 47

N-[1,3,4]Oxadiazol-2-yl-2,2-diphenyl-acetamide

The title compound, light yellow solid, m.p. 131–132° C. and MS: m/e=279.2 (M$^+$) was prepared in accordance with the general method of example 44a from [1,3,4]oxadiazol-2-ylamine and 2,2-diphenylacetic acid chloride.

EXAMPLE 48

9H-Xanthene-9-carboxylic acid (5-ethyl-[1,3,4]oxadiazol-2-yl)-amide 48a) 500.5 mg (1.64 mmol) (3,5-dimethylpyrazol-1-yl)-(9H-xanthen-9-yl)-methanone and 186.8 mg (1.64 mmol) 5-ethyl-[1,3,4]oxadiazol-2-ylamine were suspended in 1.5 ml DMF and stirred for 6 h at 130°. The reaction mixture was allowed to cool to room temperature and 5 ml of acetone were added. After stirring for 5 min, the product was filtered, washed with acetone and dried in vaccuo to yield 219.5 mg of 9H-xanthene-9-carboxylic acid (5-ethyl-[1,3,4]oxadiazol-2-yl)-amide as a white solid, m.p. 256–257° C. and MS: m/e=321.2 (M$^+$)

48b) The 5-ethyl-[1,3,4]oxadiazol-2-ylamine used in the above reaction was obtained as follows:

To a solution of 6.3 g propionic acid hydrazide (72 mmol) in 50 ml of water was added 34 g of saturated potassium bicarbonate solution (75 mmol) and a solution of 7.7 g (72 mmol) of cyanogen bromide in 60 ml of water. The temperature rises from 22° C. to 32° C. and carbon dioxide evolves. After 30 min white cristals began to appear. The white suspension is stirred for 3 h and left to stand overnight. The reaction mixture was evaporated to dryness in vacuo. The crude product is recristallised from 20 ml of water. The product is filtered, washed with a small amount of ice-cold water and dried in vacuo. One obtains 6.1 g (54 mmol, 75%) of 5-ethyl-[1,3,4]oxadiazol-2-ylamine as a white solid, m.p. 174–175° C. and MS: m/e=113.1 (M$^+$).

48c) The (3,5-dimethylpyrazol-1-yl)-(9H-xanthen-9-yl)-methanone used in the above reaction was obtained as follows: 2.6 g (11 mmol) 9-xanthenecarboxylic acid hydrazide was suspended in 2.5 ml of water. 10 ml of 2N HCl solution was added. To the thick white suspension was added 30 ml of ethanol and the suspension was heated to 65° C. and then allowed to cool to room temperature. To the resulting light yellow solution was added 1.1 g (11 mmol) of acetylacetone with vigourous stirring. The temperature rises to 30° C. with formation of white cristals after about 2 min. Stirring was continued for 15 min at room temperature and a further 15 min at 0° C. The product was filtered and washed with −20° C. ethanol. The crude product was recristallised from 15 ml of ethanol to yield 2.80 g (9.2 mmol, 84%) of (3,5-dimethylpyrazol-1-yl)-(9H-xanthen-9-yl)-methanone as white cristals, m.p. 114–115° C. and MS: m/e=304.1 (M+).

EXAMPLE 49

N-(5-Ethyl-[1,3,4]oxadiazol-2-yl)-2,2-diphenyl-acetamide

The title compound, white solid, m.p. 123–125° C. and MS: m/e=308.2 (M+H+) was prepared in accordance with the general method of example 48a from 1-(3,5-dimethyl-pyrazol-1-yl)-2,2-diphenyl-ethanone and 5-ethyl-[1,3,4]oxadiazol-2-ylamine.

The 1-(3,5-dimethyl-pyrazol-1-yl)-2,2-diphenyl-ethanone, white solid, m.p. 91–92° C. and MS: m/e=291.2 (M+H+) used in the above reaction was prepared in accordance with the general method of example 48c from 2,2-diphenylacetic acid hydrazide [Chem. Zentralblatt. 100, 2414(1929)] and acetylacetone.

EXAMPLE 50

9H-Xanthene-9-carboxylic acid (5-methyl-[1,3,4]oxadiazol-2-yl)-amide

The title compound, white solid, m.p. 261–263° C. and MS: m/e=307.1 (M+) was prepared in accordance with the general method of example 44a from 5-methyl[1,3,4]oxadiazol-2-ylamine and 9-xanthene-carboxylic acid chloride.

The 5-methyl[1,3,4]oxadiazol-2-ylamine, white solid, MS: m/e=99 (M+) used in the above reaction was prepared in accordance with the general method of example 48b from acetic acid hydrazide and cyanogen bromide.

EXAMPLE 51

N-(5-Methyl-[1,3,4]oxadiazol-2-yl)-2,2-diphenyl-acetamide

The title compound, white solid, m.p. 160–161° C. and MS: m/e=293.1 (M+) was prepared in accordance with the general method of example 44a from 5-methyl[1,3,4]oxadiazol-2-ylamine and 2,2-diphenylacetic acid chloride.

EXAMPLE 52

9H-Xanthene-9-carboxylic acid (5-methoxymethyl-[1,3,4]oxadiazol-2-yl)-amide

The title compound, white solid, m.p. 233–234° C. and MS: m/e=337.1 (M+H+) was prepared in accordance with the general method of example 48a from (3,5-dimethylpyrazol-1-yl)-(9H-xanthen-9-yl)-methanone and 5-methoxymethyl-[1,3,4]oxadiazol-2-ylamine.

The 5-methoxymethyl-[1,3,4]oxadiazol-2-ylamine, white solid, m.p. 113–114° C. and MS: m/e=129.2 (M+) used in the above reaction was prepared in accordance with the general method of example 48b from methoxyacetic acid hydrazide [J.Org.Chem.USSR, 6(1), 93(1970)] and cyanogen bromide.

EXAMPLE 53

N-(5-methoxymethyl)-[1,3,4]oxadiazol-2-yl)-2,2-diphenyl-acetamide

The title compound, white solid, m.p. 138–140° C. and MS: m/e=324.3 (M+H+) was prepared in accordance with the general method of example 44a 2,2-diphenylacetic acid chloride and 5-methoxymethyl-[1,3,4]oxadiazol-2-ylamine.

EXAMPLE 54

9H-Xanthene-9-carboxylic acid [5-(2-methoxy-ethyl)-[1,3,4]oxadiazol-2-yl]-amide

The title compound, white solid, m.p. 204° C. and MS: m/e=351.1 (M+H+) was prepared in accordance with the general method of example 44a from (3,5-dimethylpyrazol-1-yl)-(9H-xanthen-9-yl)-methanone and [5-(2-methoxy-ethyl)-[1,3,4]oxadiazol-2-yl]-amine.

The [5-(2-methoxy-ethyl)-[1,3,4]oxadiazol-2-yl]-amine, white solid, m.p. 105–106° C. and MS: m/e=143.1 (M+) used in the above reaction was prepared in accordance with the general method of example 48b from 3-methoxypropionic acid hydrazide [U.S. Pat. No. 3,441,606] and cyanogen bromide.

EXAMPLE 55

N-[5-(2-Methoxy-ethyl)-[1,3,4]oxadiazol-2-yl]-2,2-diphenyl-acetamide

The title compound, white solid, m.p. 114–115° C. and MS: m/e=338.2 (M+H+) was prepared in accordance with the general method of example 44a from 2,2-diphenylacetic acid chloride and [5-(2-methoxy-ethyl)-[1,3,4]oxadiazol-2-yl]-amine.

EXAMPLE 56

9H-Xanthene-9-carboxylic acid (5-cyclopropyl-[1,3,4]oxadiazol-2-yl)-amide

The title compound, white solid, m.p. 246–248° C. and MS: m/e=333.1 (M+H+) was prepared in accordance with the general method of example 48a from (3,5-dimethylpyrazol-1-yl)-(9H-xanthen-9-yl)-methanone and 5-cyclopropyl-[1,3,4]oxadiazol-2-ylamine [J.Med.Pharm.Chem. 5, 617(1962)].

EXAMPLE 57

N-(5-Cyclopropyl-[1,3,4]oxadiazol-2-yl)-2,2-diphenyl-acetamide

The title compound, white solid, m.p. 159–160° C. and MS: m/e=320.3 (M+H+) was prepared in accordance with the general method of example 44a from 2,2-diphenylacetic acid chloride and 5-cyclopropyl-[1,3,4]oxadiazol-2-ylamine.

EXAMPLE 58

9H-Xanthene-9-carboxylic acid (5-cyclopropylmethyl-[1,3,4]oxadiazol-2-yl)-amide

The title compound, white solid, m.p. 234–236° C. and MS: m/e=347.1(M+H+) was prepared in accordance with the general method of example 48a from (3,5-dimethylpyrazol-1-yl)-(9H-xanthen-9-yl)-methanone and 5-cyclopropylmethyl-[1,3,4]oxadiazol-2-ylamine.

The 5-cyclopropylmethyl-[1,3,4]oxadiazol-2-ylamine, white solid, m.p. 140–141° C. and MS: m/e=139 (M+) used in the above reaction was prepared in accordance with the general method of example 48b from cyclopropanecarboxylic acid hydrazide [J.Chem.Soc.Perkin Trans.2, 1844(1974)] and cyanogen bromide.

EXAMPLE 59

N-(5-Cyclopropylmethyl-[1,3,4]oxadiazol-2-yl)-2,2-diphenyl-acetamide

The title compound, white solid, m.p. 158–159° C. and MS: m/e=334.3 (M+H$^+$) was prepared in accordance with the general method of example 44a from 2,2-diphenylacetic acid chloride and 5-cyclopropylmethyl-[1,3,4]oxadiazol-2-ylamine.

EXAMPLE 60

9H-Xanthene-9-carboxylic acid (5-trifluoromethyl-[1,3,4]oxadiazol-2-yl)-amide

The title compound, white solid, m.p. 220–223° C.(decomp.), and MS: m/e=362.2 (M+H$^+$) was prepared in accordance with the general method of example 48a from (3,5-dimethylpyrazol-1-yl)-(9H-xanthen-9-yl)-methanone and 5-trifluoromethyl-[1,3,4]oxadiazol-2-ylamine [U.S. Pat. No. 2,883,391].

EXAMPLE 61

N-(5-trifluoromethyl-[1,3,4]oxadiazol-2-yl)-2,2-diphenyl-acetamide

The title compound, white solid, m.p. 149–150° C. and MS: m/e=347.2 (M$^+$) was prepared in accordance with the general method of example 44a from 5-trifluoromethyl[1,3,4]oxadiazol-2-ylamine and 2,2-diphenylacetic acid chloride.

EXAMPLE 62

9H-Xanthene-9-carboxylic acid (5-ethyl-oxazol-2-yl)-amide

The title compound, white solid, m.p. 212–213° C. and MS: m/e=320.1 (M$^+$) was prepared in accordance with the general method of example 44a from 5-ethyl-oxazol-2-ylamine [Ber. 95, 2419(1962)] and 9-xanthene-carboxylic acid chloride.

EXAMPLE 63

N-(5-Ethyl-oxazol-2-yl)-2,2-diphenyl-acetamide

The title compound, white solid, m.p. 148–149° C. and MS: m/e=307.3 (M+H$^+$) was prepared in accordance with the general method of example 44a from 5-ethyl-oxazol-2-ylamine and 2,2-diphenylacetic acid chloride.

EXAMPLE 64

9H-Xanthene-9-carboxylic acid (5-methyl-oxazol-2-yl)-amide

The title compound, white solid, m.p. 217–220° C. and MS: m/e=306.1 (M$^+$) was prepared in accordance with the general method of example 44a from 5-methyl-oxazol-2-ylamine [Ber. 95, 2419(1962)] and 9-xanthene-carboxylic acid chloride.

EXAMPLE 65

N-(5-Methyl-oxazol-2-yl)-2,2-diphenyl-acetamide

The title compound, off-white solid, m.p. 166–168° C. and MS: m/e=292.2 (M$^+$) was prepared in accordance with the general method of example 44a from 5-methyl-oxazol-2-ylamine and 2,2-diphenylacetic acid chloride.

EXAMPLE 66

9H-Xanthene-9-carboxylic acid (5-propyl-oxazol-2-yl)-amide

66a) The title compound, white solid, m.p. 203–205° C. and MS: m/e=334.1 (M$^+$) was prepared in accordance with the general method of example 44a from 5-propyl-oxazol-2-ylamine [Ber. 95, 2419(1962)] and 9-xanthene-carboxylic acid chloride.

66b) The 5-propyl-oxazol-2-ylamine used in the above reaction was obtained as follows: 21.8 g (0.132 mol) of 2-bromobutyraldehyde [Chem.Ber., 70 1898(1937)] was dissolved in 67.5 ml of a 4:3 mixture of DMF and water. Urea, 8.77 g (0.145 mol) was added with stirring. The clear colorless solution was stirred for 16 h at 105° C. The resulting light yellow solution is cooled to 0° C. and 10 ml of 45% Sodium hydroxide solution was added. The solution turns dark yellow (pH 12). 100 ml of brine is added and the solution is extracted five times with 100 ml of a 9:1 mixture of methylene chloride and methanol. The combined organic phases were concentrated to yield 15.62 g of a reddish brown oil which was purified by flash chromatography on silicagel with a 9:1 mixture of methylene chloride and methanol as eluent. One obtains 6.2 g (0.049 mol, 37%) of 5-5-propyl-oxazol-2-ylamine as a yellow oil which was directly used without further purification, MS: m/e=126.1 (M$^+$).

EXAMPLE 67

2,2-Diphenyl-N-(5-propyl-oxazol-2-yl)-acetamide

The title compound, white solid, m.p. 122° C. and MS: m/e=320.2 (M$^+$) was prepared in accordance with the general method of example 44a from 5-propyl-oxazol-2-ylamine and 2,2-diphenylacetic acid chloride.

EXAMPLE 68

9H-Xanthene-9-carboxylic acid (4-methyl-oxazol-2-yl)-amide

The title compound, light yellow solid, m.p. 219–222° C. and MS: m/e=306.1 (M$^+$) was prepared in accordance with the general method of example 48a from (3,5-dimethylpyrazol-1-yl)-(9H-xanthen-9-yl)-methanone and 5-methyl-oxazol-2-ylamine [DE 2459380].

EXAMPLE 69

N-(4-Methyl-oxazol-2-yl)-2,2-diphenyl-acetamide

The title compound, white solid, m.p. 209–211° C. and MS: m/e=306.1 (M$^+$) was prepared in accordance with the general method of example 48a from (3,5-dimethylpyrazol-1-yl)-(9H-xanthen-9-yl)-methanone and 5-methyl-oxazol-2-ylamine.

EXAMPLE 70

N-(3-Methyl-[1,2,4]oxadiazol-5-yl)-2,2-diphenyl-acetamide

The title compound, white solid, m.p. 215° C. and MS: m/e=293 (M$^+$) was prepared in accordance with the general method of example 44a from 3-methyl-[1,2,4]oxadiazol-5-ylamine (Helv. Chim. Acta, 49(1966), 1430–1432) and 2,2-diphenylacetic acid chloride.

EXAMPLE 71

9H-Xanthene-9-carboxylic acid (3-methyl-[1,2,4]oxadiazol-5-yl)-amide

The title compound, white solid, m.p. 208° C. and MS: m/e=307 (M$^+$) was prepared in accordance with the general method of example 44a from 3-methyl-[1,2,4]oxadiazol-5-ylamine and 9H-xanthene-carboxylic acid chloride.

EXAMPLE 72

N-(3-Cyclopropyl-[1,2,4]oxadiazol-5-yl)-2,2-diphenyl-acetamide

The title compound, white solid, m.p. 163° C. and MS: m/e=219 (M$^+$) was prepared in accordance with the general method of example 44a from 3-cyclopropyl-[1,2,4]oxadiazol-5-ylamine (Helv. Chim. Acta, 49(1966), 1430–1432) and 2,2-diphenylacetic acid chloride.

EXAMPLE 73

9H-Xanthene-9-carboxylic acid (3-cyclopropyl-[1,2,4]oxadiazol-5-yl)-amide

The title compound, white solid, m.p. 275° C. and MS: m/e=333 (M$^+$) was prepared in accordance with the general method of example 44a from 3-cyclopropyl-[1,2,4]oxadiazol-5-ylamine and 9H-xanthene-carboxylic acid chloride.

EXAMPLE 74

N-(5-Methyl-[1,2,4]oxadiazol-3-yl)-2,2-diphenyl-acetamide

The title compound, white solid, m.p. 153° C. and MS: m/e=293 (M$^+$) was prepared in accordance with the general method of example 44a from 5-methyl-[1,2,4]oxadiazol-3-ylamine (EP 413545) and 2,2-diphenylacetic acid chloride.

EXAMPLE 75

9H-Xanthene-9-carboxylic acid (5-methyl-[1,2,4]oxadiazol-3-yl)-amide

The title compound, white solid, m.p. 186° C. and MS: m/e=307 (M$^+$) was prepared in accordance with the general method of example 44a from 5-methyl-[1,2,4]oxadiazol-3-ylamine and 9H-xanthene-carboxylic acid chloride.

Table 1 sets forth the substituents for each compound of the previously described Examples

TABLE 1

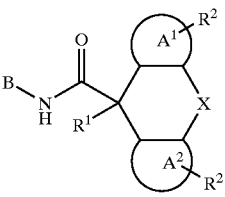

B

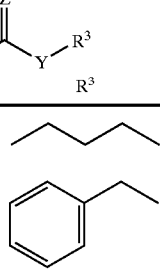

| A$^1$/A$^2$ | X | R$^1$ | R$^2$ | Z | Y | R$^3$ | heterocycle | Expl. |
|---|---|---|---|---|---|---|---|---|
| phenyl | H/H | H | H | O | O | 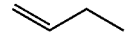 | — | 1 |
| phenyl | H/H | H | H | O | O |  | — | 2 |
| phenyl | H/H | H | H | O | O |  | — | 3 |
| phenyl | H/H | H | H | O | O |  | — | 4 |
| phenyl | H/H | H | H | O | O |  | — | 5 |
| phenyl | O | H | H | O | O | 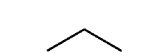 | — | 6 |
| phenyl | O | H | Br | O | O | 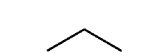 | — | 7 |
| phenyl | O | H | H | O | O |  | — | 8 |
| phenyl | H/H | H | H | O | O | 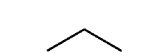 | — | 9 |

TABLE 1-continued
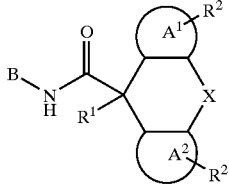
| | | | | | | B | | |
|---|---|---|---|---|---|---|---|---|
| | | | | | | 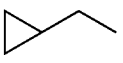 | | |
| A¹/A² | X | R¹ | R² | Z | Y | R³ | heterocycle | Expl. |
| phenyl | H/H | H | H | O | O | 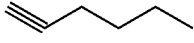 | — | 10 |
| phenyl | H/H | H | H | O | O | 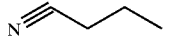 | — | 11 |
| phenyl | H/H | H | H | O | O | 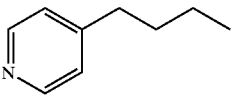 | — | 12 |
| phenyl | H/H | H | H | O | O | 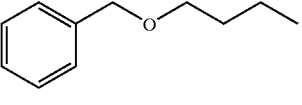 | — | 13 |
| phenyl | H/H | H | H | O | O | 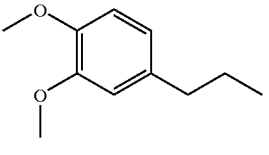 | — | 14 |
| phenyl | H/H | H | H | O | O | 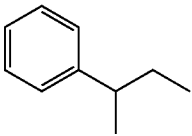 | — | 15 |
| phenyl | H/H | H | H | O | O |  | — | 16 |
| phenyl | H/H | H | H | O | O | 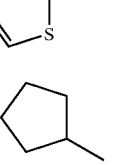 | — | 17 |
| phenyl | H/H | H | H | O | O | 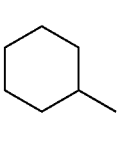 | — | 18 |
| phenyl | H/H | H | H | O | O | 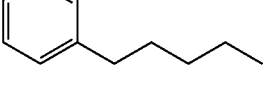 | — | 19 |
| phenyl | H/H | H | H | O | O |  | — | 20 |

TABLE 1-continued
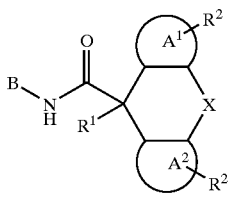
I
| A¹/A² | X | R¹ | R² | Z | Y | R³ | heterocycle | Expl. |
|---|---|---|---|---|---|---|---|---|
| phenyl | H/H | H | H | O | O | 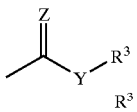 | — | 21 |
| phenyl | H/H | H | H | O | O | 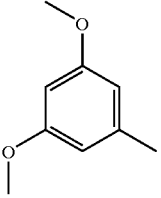 | — | 22 |
| phenyl | H/H | CH₃ | H | O | O | 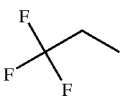 | — | 23 |
| phenyl | H/H | CH₃ | H | O | O |  | — | 24 |
| phenyl | H/H | CH₃ | H | O | O |  | — | 25 |
| phenyl | H/H | CH₃ | H | O | O | 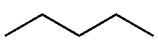 | — | 26 |
| phenyl | H/H | CH₃ | H | O | O | 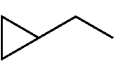 | — | 27 |
| phenyl | H/H | CH₃ | H | O | O | 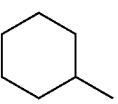 | — | 28 |
| phenyl | H/H | CH₃ | H | O | O | 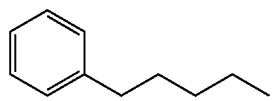 | — | 29 |
| phenyl | S | H | H | O | O | 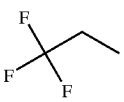 | — | 30 |
| phenyl | S | H | H | — | — | — |  | 31 |
| phenyl | S | H | H | O | O | 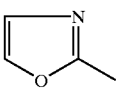 | — | 32 |
| phenyl | O | H | H | — | — | — |  | 33 |

TABLE 1-continued
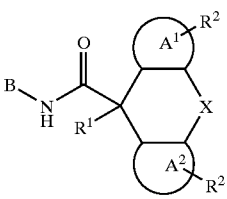
I
B
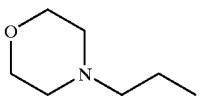
| A¹/A² | X | R¹ | R² | Z | Y | R³ | heterocycle | Expl. |
|---|---|---|---|---|---|---|---|---|
| phenyl | H/H | H | H | O | O | 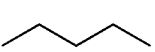 | — | 34 |
| phenyl | H/H | H | H | O | S | 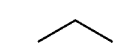 | — | 35 |
| pyridyl/phenyl | H/H | H | 3-CF₃ 5-Cl | O | O | 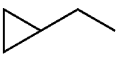 | — | 36 |
| phenyl | O | H | H | O | O |  | — | 37 |
| phenyl | O | H | CF₃ in A2 | O | O |  | — | 38 |
| phenyl | H/H | H | H | O | a bond |  | — | 39 |
| phenyl | O | H | H | O | a bond |  | — | 40 |
| phenyl | H/H | H | H | O | a bond | 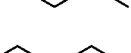 | — | 41 |
| phenyl | H/H | H | H | O | a bond |  | — | 42 |
| phenyl | H/H | H | H | O | a bond | 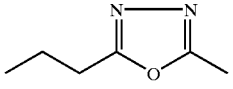 | — | 43 |
| phenyl | O | H | H | — | — | — | 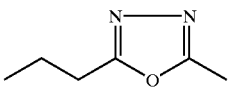 | 44 |
| phenyl | H/H | H | H | — | — | — | 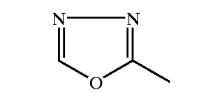 | 45 |
| phenyl | O | H | H | — | — | — | 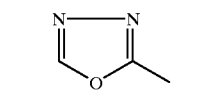 | 46 |
| phenyl | H/H | H | H | — | — | — | 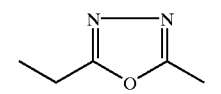 | 47 |
| phenyl | O | H | H | — | — | — |  | 48 |

TABLE 1-continued

| A¹/A² | X | R¹ | R² | Z | Y | R³ | heterocycle | Expl. |
|---|---|---|---|---|---|---|---|---|
| phenyl | H/H | H | H | — | — | — | 2-ethyl-5-methyl-1,3,4-oxadiazole | 49 |
| phenyl | O | H | H | — | — | — | 2,5-dimethyl-1,3,4-oxadiazole | 50 |
| phenyl | H/H | H | H | — | — | — | 2,5-dimethyl-1,3,4-oxadiazole | 51 |
| phenyl | O | H | H | — | — | — | 2-(methoxymethyl)-5-methyl-1,3,4-oxadiazole | 52 |
| phenyl | H/H | H | H | — | — | — | 2-(methoxymethyl)-5-methyl-1,3,4-oxadiazole | 53 |
| phenyl | O | H | H | — | — | — | 2-(2-methoxyethyl)-5-methyl-1,3,4-oxadiazole | 54 |
| phenyl | H/H | H | H | — | — | — | 2-(2-methoxyethyl)-5-methyl-1,3,4-oxadiazole | 55 |
| phenyl | O | H | H | — | — | — | 2-cyclopropyl-5-methyl-1,3,4-oxadiazole | 56 |
| phenyl | H/H | H | H | — | — | — | 2-cyclopropyl-5-methyl-1,3,4-oxadiazole | 57 |
| phenyl | O | H | H | — | — | — | 2-(cyclopropylmethyl)-5-methyl-1,3,4-oxadiazole | 58 |
| phenyl | H/H | H | H | — | — | — | 2-(cyclopropylmethyl)-5-methyl-1,3,4-oxadiazole | 59 |

TABLE 1-continued
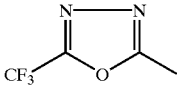
I
| A¹/A² | X | R¹ | R² | Z | Y | R³ | heterocycle | Expl. |
|---|---|---|---|---|---|---|---|---|
| phenyl | O | H | H | — | — | — | 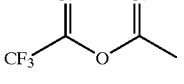 | 60 |
| phenyl | H/H | H | H | — | — | — | 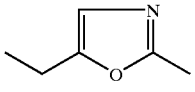 | 61 |
| phenyl | O | H | H | — | — | — | 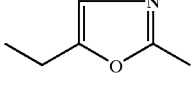 | 62 |
| phenyl | H/H | H | H | — | — | — | 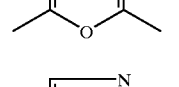 | 63 |
| phenyl | O | H | H | — | — | — | 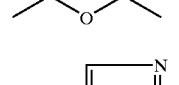 | 64 |
| phenyl | H/H | H | H | — | — | — |  | 65 |
| phenyl | O | H | H | — | — | — |  | 66 |
| phenyl | H/H | H | H | — | — | — | 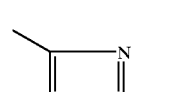 | 67 |
| phenyl | O | H | H | — | — | — | 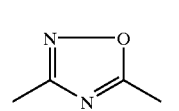 | 68 |
| phenyl | H/H | H | H | — | — | — |  | 69 |
| phenyl | H/H | H | H | — | — | — |  | 70 |

TABLE 1-continued

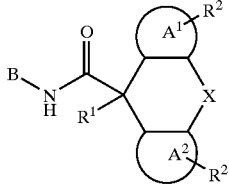

| A¹/A² | X | R¹ | R² | Z | Y | R³ | heterocycle | Expl. |
|---|---|---|---|---|---|---|---|---|
| phenyl | O | H | H | — | — | — | 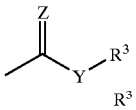 | 71 |
| phenyl | H/H | H | H | — | — | — | 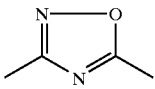 | 72 |
| phenyl | O | H | H | — | — | — | 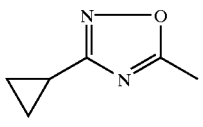 | 73 |
| phenyl | H/H | H | H | — | — | — | 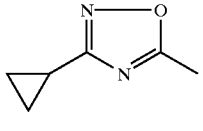 | 74 |
| phenyl | O | H | H | — | — | — | 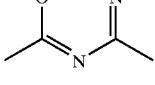 | 75 |

H/H for X in the above Table 1 denotes two hydrogen atoms, not forming a brigde.

EXAMPLE A

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

| | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

| mg/Capsule | |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of formula I:

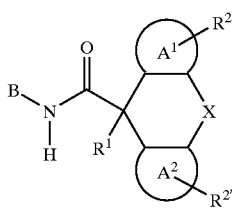

I wherein
$A^1$ and $A^2$ are phenyl;
$R^1$ is hydrogen or lower alkyl;
$R^2$ and $R^{2'}$ are independently selected from the group consisting of hydrogen, lower alkyl, lower alkoxy, halogen and trifluoromethyl;
X signifies two hydrogen atoms not forming a bridge; and
B is a 5-membered heterocyclic group of formulae:

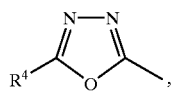

(a)

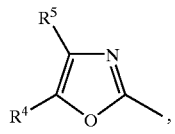

(b)

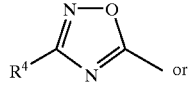

(c)

or

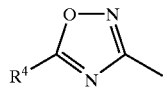

(d)

wherein
$R^4$ and $R^5$ are independently selected from the group consisting of hydrogen, lower alkyl, lower alkoxy, lower cycloalkyl, cyclopentyl, lower alkyl-cyclopentyl, cyclohexyl, lower alkyl-cyclohexyl and trifluoromethyl, with the proviso that at least one of R4 or R5 has to be hydrogen;
or a pharmaceutically acceptable salt thereof.

2. A compound of formula IB in accordance with claim 1, N-(5-ethyl-oxazol-2-yl)-2,2-diphenyl-acetamide.

3. A compound of formula IB in accordance with claim 1, N-(5-methyl-oxazol-2-yl)-2,2-diphenyl-acetamide.

4. A compound of formula IB in accordance with claim 1, 2,2-diphenyl-N-(5-propyl-[1,3,4]oxadiazol-2-yl)-acetamide.

5. A compound of formula IB in accordance with claim 1, N-[5-(2-methoxy-ethyl)-[1,3,4]oxadiazol-2-yl]-2,2-diphenyl-acetamide.

6. A compound of formula IB in accordance with claim 1, N-(3-methyl-[1,2,4]oxadiazol-5-yl)-2,2-diphenyl-acetamide.

7. A compound of formula IB in accordance with claim 1, N-(3-cyclopropyl-[1,2,4]oxadiazol-5-yl)-2,2-diphenyl-acetamide.

8. A compound of formula IB in accordance with claim 1, N-(5-methyl-[1,2,4]oxadiazol-3-yl)-2,2-diphenyl-acetamide.

9. The compound of claim 1 of formula I wherein the compound is N-[1,3,4]Oxadiazol-2-yl-2,2-diphenyl-acetamide.

10. The compound of claim 1 of formula I wherein the compound is N-(5-Ethyl-[1,3,4]oxadiazol-2-yl)-2,2-diphenyl-acetamide.

11. The compound of claim 1 of formula I wherein the compound is N-(5-Cyclopropyl-[1,3,4]oxadiazol-2-yl)-2,2-diphenyl-acetamide.

12. The compound of claim 1 of formula I wherein the compound is N-(5-Cyclopropylmethyl-[1,3,4]oxadiazol-2-yl)-2,2-diphenyl-acetamide.

13. The compound of claim 1 of formula I wherein the compound is N-(4-Methyl-oxazol-2-yl)-2,2-diphenyl-acetamide.

14. The compound of claim 1 of formula I wherein the compound is N-(5-Methyl-[1,3,4]oxadiazol-2-yl)-2,2-diphenyl-acetamide.

15. The compound of claim 1 of formula I wherein the compound is N-(5-trifluoromethyl-[1,3,4]oxadiazol-2-yl)-2,2-diphenyl-acetamide.

16. The compound of claim 1 of formula I wherein the compound is 2,2-Diphenyl-N-(5-propyl-oxazol-2-yl)-acetamide.

17. A process for the manufacture of a compound according to claim 1 comprising reacting a compound of formula:

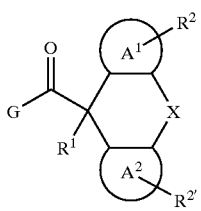

IV with a heterocyclic compound of formula:

B—$NH_2$

IX to give a compound of formula:

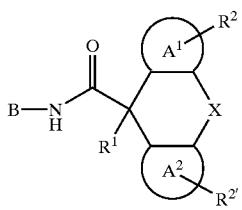

IB (a–d)

wherein B is a 5-membered heterocycle of the formulae:

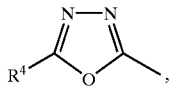
(a)

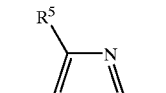
(b)

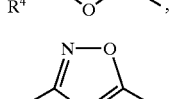
or
(c)

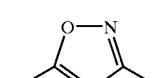
(d)

and wherein G is a leaving group and the remaining substituents have the significances given in claim 1.

18. A pharmaceutical composition comprising a therapeutically effective amount of the compound according of formula I:

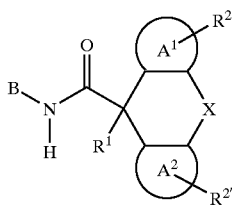

I wherein

A$^1$ and A$^2$ are phenyl;

R$^1$ is hydrogen or lower alkyl;

R$^2$ and R$^{2'}$ are independently selected from the group consisting of hydrogen, lower alkyl, lower alkoxy, halogen and trifluoromethyl;

X signifies two hydrogen atoms not forming a bridge; and

B is a 5-membered heterocyclic group of formulae:

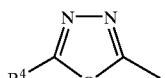
(a)

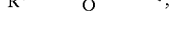
(b)

-continued

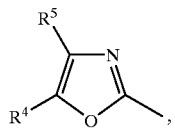
(b)

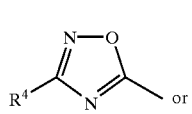
or
(c)

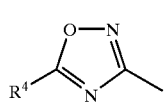
(d)

wherein

R$^4$ and R$^5$ signifies hydrogen, lower alkyl, lower alkoxy, lower cycloalkyl, cyclopentyl, lower alkyl-cyclopentyl, cyclohexyl, lower alkyl-cyclohexyl or trifluoromethyl, with the proviso that at least one of R4 or R5 has to be hydrogen; or a pharmaceutically acceptable salt thereof and a pharmaceutically inert carrier.

19. A method of treating neurological disorders comprising administering an effective amount of a compound of the formula I to a person in need of such treatment:

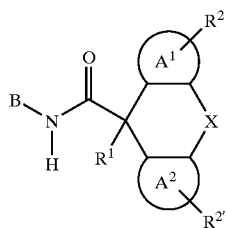

I wherein

A$^1$ and A$^2$ are phenyl;

R$^2$ and R$^{2'}$ are independently selected from the group consisting of hydrogen, lower alkyl, lower alkoxy, halogen and trifluoromethyl;

X signifies two hydrogen atoms not forming a bridge; and

B is a 5-membered heterocyclic group of formulae:

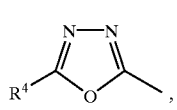
(a)

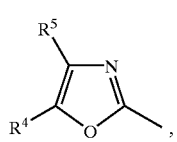
(b)

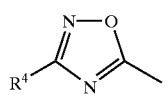 (c)
or
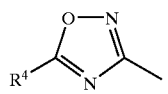 (d)
wherein
R⁴ and R⁵ signifies hydrogen, lower alkyl, lower alkoxy, lower cycloalkyl, cyclopentyl, lower alkyl-cyclopentyl, cyclohexyl, lower alkyl-cyclohexyl or trifluoromethyl, with the proviso that at least one of R4 or R5 has to be hydrogen, or a pharmaceutically acceptable salt thereof.
* * * * *

UNITED STATES PATENT AND TRADEMARK OFFICE
CERTIFICATE OF CORRECTION

PATENT NO.    : 6,596,743 B2
DATED         : July 22, 2003
INVENTOR(S)   : Bleicher et al It is certified that error appears in the above-identified patent and that said Letters Patent is hereby corrected as shown below:

Column 39,
Line 37, "$R^2$ and $R^2$" should read -- $R^2$ and $R^{2'}$ --

Signed and Sealed this

Fifteenth Day of June, 2004

JON W. DUDAS
*Acting Director of the United States Patent and Trademark Office*